(12) United States Patent
Dobson et al.

(10) Patent No.: US 7,560,234 B2
(45) Date of Patent: Jul. 14, 2009

(54) DETECTION OF OCHRATOXIN A PRODUCING FUNGI

(75) Inventors: Alan Dobson, Cork (IE); John O'Callaghan, Mallow (IE)

(73) Assignee: University College Cork—National University Of Ireland Cork, Cork (IE)

( * ) Notice: Subject to any disclaimer, the term of this patent is extended or adjusted under 35 U.S.C. 154(b) by 172 days.

(21) Appl. No.: 11/201,194

(22) Filed: Aug. 11, 2005

(65) Prior Publication Data

US 2006/0019306 A1    Jan. 26, 2006

Related U.S. Application Data

(63) Continuation of application No. PCT/IE2004/000020, filed on Feb. 12, 2004.

(30) Foreign Application Priority Data

Feb. 12, 2003    (IE)    ................... 2003/0095

(51) Int. Cl.
  *C12Q 1/68* (2006.01)
  *C12P 19/34* (2006.01)
  *C07H 21/02* (2006.01)
  *C07H 21/04* (2006.01)

(52) U.S. Cl. .............. 435/6; 435/91.2; 536/23.1; 536/23.7; 536/23.74; 536/24.32; 536/24.33

(58) Field of Classification Search ............... None
  See application file for complete search history.

(56) References Cited

OTHER PUBLICATIONS

Elmholt et al. Mycopathologia. 1999. 147: 67-81.*
Accensi et al. Antonic Leeuwenhoek. 2001. 79: 365-3.*
Gene et al. Antonic Leeuwenhoek. 1995. 70: 49-57.*
Burdaspal et al, 1998, Alimentaria 35, 1998, pp. 103-109, Ochratoxin A in roasted and soluble coffees marketed in Spain.
Burdaspal et al, Alimentaria 36, 1999, pp. 107-113, Ochratoxin A in wines and grape products originated from Spain and other . . .
Dietrich et al, Food and Chemical Toxicology, vol. 33, Issue 5, May 1995, pp. 341-355, The Occurrence of Ochratoxin A in Coffee.
Edwards et al, MYCOL. RES. 106, 2002, pp. 1005-1025, PCR based detection and quantification of mycotoxigenic fungi.
Geisen, APPLNS. OF PCR IN MYCOLOGY, 1998, pp. 243-246, PCR methods for the detection of mycotoxin producing fungi.
Jorgenson, Food Addit. Contam. 16, 1998, pp. 75-78, Survey of pork, poultry, coffee, beer and pulses for ochratoxin A.
Kuiper-Goodman, Food Addit. Contam. 13 (Suppl), 1996, pp. S53-S57, Risk assessment of ochratoxin A: an update.
Pittet, Rev. Mded. Vet. 149, 1998, pp. 479-492, Natural occurrence of mycotoxins in food and feeds —an updated review.
Scientific Committee for Food 35th Series, 1996, Opinion on aflatoxin, ochratoxin A and patulin, expressed on 23rd . . .
Visconti et al, Journal of Chromatography A, vol. 864, Issue 1, Dec. 9, 1999, pp. 89-101, Determination of ochratoxin A in wine . . .
Visconti, Journal of Chromatography A 888, 2000, pp. 321-326, Determination of ochratoxin A in domestic and imported beers . . .
Wolff et al, Arch. Lebensmittelhyg. 51, 2000, pp. 81-128, Ochratoxin A: contamination of foods and consumer exposure.
Zimmerli et al, Food Addit. Contam. 13, 1996, pp. 655-668, Ochratoxin A in table wine and grape juice: occurrence and . . .

* cited by examiner

*Primary Examiner*—Carla Myers
(74) *Attorney, Agent, or Firm*—Jacobson Holman PLLC

(57) ABSTRACT

Nucleotide or amino acid sequences that may be used in the detection and/or identification for an ochratoxigenic fungus or in the construction of an atoxigenic strain of an ochratoxigenis fungus. The fungus may be of the genus *Aspergillus*, species *carbonarius, niger, alliaceus,* or *foetidux*. The fungus may also be of the genus *Penicillium*, species *verrucosum*.

6 Claims, 4 Drawing Sheets

Figure 6 (*Aspergillus foetidus* RT-PCR)
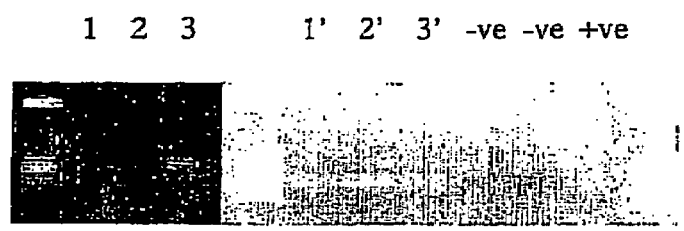
Figure 7. OTA Production by Aspergillus foetidus
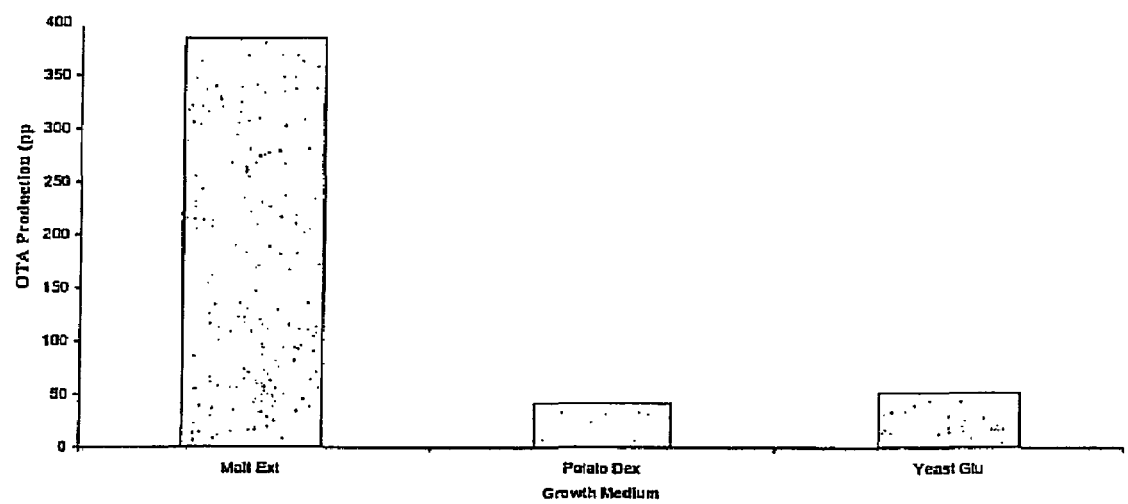
Figure 8 (*Aspergillus niger* RT-PCR)
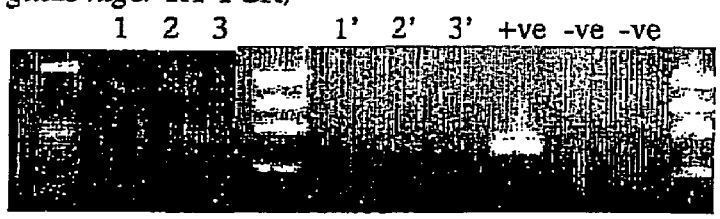

SEQUENCE LISTING

<160> NUMBER OF SEQ ID NOS: 29

<210> SEQ ID NO 1
<211> LENGTH: 630
<212> TYPE: DNA
<213> ORGANISM: Aspergillus ochraceus
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (373)..(373)
<223> OTHER INFORMATION: n is a, c, g, or t
<220> FEATURE:
<221> NAME/KEY: misc_feature
<222> LOCATION: (382)..(382)
<223> OTHER INFORMATION: n is a, c, g, or t

<400> SEQUENCE: 1

```
ggccgcggga attcgattgg ccgcccgggc aggnactttt tttttttttt tttttttcaa      60
tttcaatctg accntntatt tgngtgtagt tgacagtaaa tcggagaatt aattaaatac     120
aaaatcagga gaacgggatg ccaaaacagt gaggcgaaag agtgaggcga cacaactcaa     180
aactgccatc tccgatttga atcgaaccaa ggaataaata atcacctgca cccaattcac     240
aggagcaatg tcactctggg acctatccag gactgaaaca ataactcaat aaatcgatgc     300
tatctcgtag ctgcttgccc agttggtcca ttcaaacctg gcgagtagat catctaggaa     360
gctttaggcg tanactgtga anaagagcgc gcgagacaag tggtataacg ggaataaaca     420
caacattccg cacatcctta ccgatgcact ggagtcaact tcaccttcaa tggatccttt     480
tcccagatgt tgtaagactt ttggttatcc catccctcgc attcttcttc aaatgccagg     540
tcaaagttcc acagtagctt cacggcaatc agacgcattt cggcataagc aagattcctt     600
tccgaggcag ttccctgggc ccgtaggaaa                                      630
```

<210> SEQ ID NO 2
<211> LENGTH: 371
<212> TYPE: DNA
<213> ORGANISM: Aspergillus ochraceus
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t

<400> SEQUENCE: 2

```
accgctatgc gcggagaagt cagcgtgggc tattgtcgnt tttnttgcga ttctgaaagc     60
tggagctgcc tgtacnccnc tcgagccgtc tcatccgcga gatagattga aaaacttgat    120
tcgagcctgt ggtgcaacag ccgttgtggt aacggcccca cacgcctcaa tgcttgagat    180
ggagggaatt gatgtcgtcg tcgtttcttc caagactgta tcgtctcggg atgaaggttt    240
ggcttgtgta gccaatgcca cggtcactcc acgatcccca gcctttctaa tgtggacatc    300
tggaagcacg ggaaacccca aaggcgtcgt tctggaacat gcagctctgt acctgcccgg    360
gcggccgctc g                                                         371
```

<210> SEQ ID NO 3
<211> LENGTH: 666
<212> TYPE: DNA
<213> ORGANISM: Aspergillus ochraceus
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t

<400> SEQUENCE: 3

```
accgatgaac attccaacga ctcgcccgaa tcgtgggntg gcgagggccc cgacagttct     60
cccgtcgccg acgtcgaggt gaagatccac gacatttccc atccgctcgc catggcctcc   120
gccaaagcct tccacttcaa tatggtcgct cctcacgatg cggacctgtc gatgggagac   180
gtaacgccca aggtcgaaga agtggacgac gcggatgatt tacaaagtat caaacctatg   240
ggtgtggatc cgctggccaa tgcggactct actcatctgg attccacggc tcttcccgtc   300
aacgttccac ggaaacgtgg acgaccacgc aaacatcctc ttccagctcc cggaggtcaa   360
gtgaaaatca ccaaaggtcg atccaagacg ggctgcataa cgtgtcgacg acggaagaag   420
aaatgcgacg agaccaagcc agcgtgccta aattgtcaga aaaatgccgt cgtgtgtgaa   480
ggttatccgc caaggagat ctggaagagt gggaaacaga agcaggaaga tgcagctgcc    540
cgatgccaga cgatgatctc tcgtgccctc ctttctgatc gatggaatcg aaagcgatat   600
tgaccgacgc tttctggatc attttgggac ctcgggcgng ancaccttat cactaatgaa   660
tttgcg                                                              666
```

<210> SEQ ID NO 4
<211> LENGTH: 844
<212> TYPE: DNA
<213> ORGANISM: Aspergillus ochraceus
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (535)..(535)
<223> OTHER INFORMATION: n is a, c, g, or t
<220> FEATURE:
<221> NAME/KEY: misc_feature
<222> LOCATION: (595)..(595)
<223> OTHER INFORMATION: n is a, c, g, or t
<220> FEATURE:

```
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (631)..(631)
<223> OTHER INFORMATION: n is a, c, g, or t
<220> FEATURE:
<221> NAME/KEY: misc_feature
<222> LOCATION: (637)..(637)
<223> OTHER INFORMATION: n is a, c, g, or t
<220> FEATURE:
<221> NAME/KEY: misc_feature
<222> LOCATION: (718)..(718)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (731)..(731)
<223> OTHER INFORMATION: n is a, c, g, or t
<220> FEATURE:
<221> NAME/KEY: misc_feature
<222> LOCATION: (745)..(745)
<223> OTHER INFORMATION: n is a, c, g, or t
<220> FEATURE:
<221> NAME/KEY: misc_feature
<222> LOCATION: (748)..(748)
<223> OTHER INFORMATION: n is a, c, g, or t
<220> FEATURE:
<221> NAME/KEY: misc_feature
<222> LOCATION: (754)..(754)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (779)..(779)
<223> OTHER INFORMATION: n is a, c, g, or t
<220> FEATURE:
<221> NAME/KEY: misc_feature
<222> LOCATION: (794)..(794)
<223> OTHER INFORMATION: n is a, c, g, or t
<220> FEATURE:
<221> NAME/KEY: misc_feature
<222> LOCATION: (797)..(797)
<223> OTHER INFORMATION: n is a, c, g, or t
<220> FEATURE:
<221> NAME/KEY: misc_feature
<222> LOCATION: (810)..(811)
<223> OTHER INFORMATION: n is a, c, g, or t
<220> FEATURE:
<221> NAME/KEY: misc_feature
<222> LOCATION: (814)..(814)
<223> OTHER INFORMATION: n is a, c, g, or t

<400> SEQUENCE: 4
cgaggaatgc gaacgctggg gttcacttcg atcaggncac ctttagcggt gtgaatgtag      60
atctgaagtt taccggcctt gttgacgggc gaatcgagga gggtgaggag acactgatgg     120
gtaatatccg gtcgagcctc gctgatgtct ctgttcatct tgcgcatcac accgatatgc     180
tcgtcgctgt tgagcaagga gtatttctca tcacggttgg tgccgctgcg tccgccatga     240
gaggcgcgga aagtttccaa gcttgcatga gacaggacga cgatcaagcg ctgggtctct     300
ttatcgtggg cagagatggg gacatgttgc tcggcgacca actgaggcag ttcgggagga     360
gggcaagact gggtcctggc acgctttctc cttcctgcta cttgaacaga atccgacata     420
ttgaaccgat gaaccaattg aagacttttt ttatataaaa taaaaaagga gagtattata     480
tgtaattcga gactcgggac cgataagaag aatcgaggga ggaggagaaa agacngacga     540
```

-continued

```
cagacgattg agaagagcga caaacggtaa taaaggaaga tcccgagagg cgcanagaga      600
angaagcggt tgcaggataa ctgcagtcca ngatganggg attcaagggg gatgtttgtc      660
gcttgcttaa ccccggactg ccgcgcgtca atatatgatc cgcgctgagc acttgaantc      720
accgtganta ntggtttgga ctaantgnga atgnantgtc tggaatgtct catcccaana      780
cgactaagag cggnatngca tcatatgtgn ntcntcacga cggcattata ccaccggagg      840
tgtg                                                                   844

<210> SEQ ID NO 5
<211> LENGTH: 582
<212> TYPE: DNA
<213> ORGANISM: Aspergillus ochraceus
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t

<400> SEQUENCE: 5
cagactgtca ttgtatgggc tgtcgtttca gttcccnttn ncacaatggt aatgtattca       60
tgaagaaccc tancctcggt gacatcaggg gtatcggggg ctttggcgac catttcctgg      120
aaaagcgccg gttcctggga gagtctgttt ttctcaaagt ctagcttcgc ctcttcttcg      180
ttctcccaca tgaagttcac ctcctgggca catttcattc gaaatgcaat cacagggagc      240
aacttgggat aaacccgctt gacccacttc attcccatgc tcgccagaag agggaaaaat      300
cccggaagat gccgggcgat cattccgatc tcgacgaggt tcttaattgt ttcactccat      360
atagggacca tctcggggtc gtctaggtag ttgaacgcac ggaagctcgt ataagaggtg      420
ataatgtcgg cggtgaaaca gttgaatgcg acgtctactt ttaggggctc cccgagtga      480 gcatactcgc tcaaccgggt attcagtttc tgaagtttac tctgaatgag tgactgaata      540
cgctgtacct cggccgcgac cacgctaatc actagtgaat tc                         582

<210> SEQ ID NO 6
<211> LENGTH: 670
<212> TYPE: DNA
<213> ORGANISM: Aspergillus ochraceus

<400> SEQUENCE: 6
actatccact tgatggaatt cacaacttct tctccctgtt tccctctcta aagccaaaaa       60
cagaccccgc aatctttctc atctggattt cttccgaccc ctccgtaatt cgataccgtc      120
taaaatgacg ataaatgtgc tcgaatagat aatggcgcga gtatccatct cccccgtgga      180
tctgaatcgc cctatccgcc gcctcgcaaa ctaatctatt agcccaaaaa ttacacattg      240
cgacctcatc gcccagtttc ttctcgatct ccacccaagg ctttctcccc tcgctctccg      300
cctccccagc tacctgatcc atgtccacac tagtcttcag aatcagcagt cggagcatct      360
cgacctgcgt caccaactca acgactggga actgaatgcc ctggttctcg acagaccct      420 ttccgcccca aattttcctg ttcttcgcgc gctcaatgct ccgatccagg cagaactttg      480
ccgcaccgca tgaattggcc gcctgtcgca gtcgattttc atacatgaat gtctgcgcga      540
```

-continued

```
tcgctagtcc ctcgccaaca gttcctagca cagcctcaat tgacacaaaa acccgatcta      600
aatttacggt cgcatgatcg gtcggcatat tcatcggcca ttcgtaacta cgatttcacc      660
cccttcgtct                                                              670
```

<210> SEQ ID NO 7
<211> LENGTH: 2179
<212> TYPE: DNA
<213> ORGANISM: Aspergillus ochraceus
<400> SEQUENCE: 7

```
tcgaaggcaa ttgccaatgg agaatcaaat ggcacaagtc gcattccact tcgcagttgg       60
atcccggaaa gccgtgtttt cattctttcg gcatttgatg aggctggttt ggaccgaaac      120
gcgatgtcca tgatatctta cctcgaatca ttgaaactct ccggagatcc tgatctggaa      180
gaagcgttca tgagcgacct atgtcataca ctaaacgcaa aacgcacaat gtttgattgg      240
cgcagctacc acgtcgctga caccatcgaa aacctaaaaa agtcgcttcg gaatatccgc      300
ccatatcgtc gatcgacaag ctcgaaagcc gtccgtttta tattcacggg ccaaggagcg      360
aattgggctg gcatggccca agatctctta ctttacccat tgtttcgaca acggatccaa      420
gaagctgcaa tgttcttggg agaaattgga tgcgagtggg atctttatgg tatagtcttg      480
tccattcctt ttcttaatcc tttttttttgt ctttatttcc tcctctctcc cctcaaatta     540
ttgggtgacg ccgaataacc aaaaatttag accgaatcag ctcacagcac ggtgacctaa      600
acgagcccac ttttgcgcaa tcctcctgtg tagccgtgca gattgcgttg gtagacttgc      660
ttcatagctg gaaggtgacg ccaacaacgg tagtaggaca ttcgtccggc gaaattgcag      720
cagcgtattg tgcgggaaaa atctcacgtc aagcagcatg gaaaatcgcc tactgtcgag      780
gacaggtttg tgcaaaacag acacacgaag atggccgcat gctcgcagcg gctatgcctg      840
cacaggaatt ggaacgactg ttagctcgtt tgaacaaagg tctatgctct gcggttcagg      900
tcggatgtta acagccccc aagaacttga ccctgacagg ccaacacgag agcattcttc       960
aggtcaaggg cgagttagac gaagcgggtg tgctaaaccg tttacttcca gttaaggttg     1020
cttatcactc gaaattcatg cgagaagtcg ctccagagta cttagagctc ctcggggacc     1080
tggatttcgg tgacaagatg accgaccatg ccaaagttac tatgatatcc tcggttacgg     1140
gacgacatgc actcgcaggg gaggttgaga gtccttcgta ctgggttgat aatctgatct     1200
cacctgtccg tttctctact gcgcttctca catccatgca aacacaaagt caaaagtcac     1260
ccagcgataa cgcactgatt gaaatcggac ctcattctac tctccgcacc gccatcaatg     1320
agacccttgc ggatcaacct acactgcagc cgtttcaata cggtagtctg ctcaagcgat     1380
atgagactga cggaacgaca agcctgcgca cattcgattt gttgacctct tatggctatg     1440
atgttagcct ggcttctgtt aatgatcctc gatcaaaaat taagaaagct cctcatatga     1500
taacggatct tccgccttac tcctttgacc actcacggtc ggttcgcggc cagtctcgaa     1560
gaatcaaaaa catcaagttt ccagcgtacg aacgccatga gctccttggt gcgccagttg     1620
aagatacaaa caaatttgag caacgatgga ggaacatcat tagaccggac gatattacat     1680
ggttgcgcat gaacagagtg agtacttcct ataaaattat gagcccatct aacgtgagcc     1740
agatggatga agtatccat ttccccgag tcgcctacct tttgatgcc atggaggcca       1800 taatgcagcg aactgggatg acagaatgtg tcaccggcat taggattggc aatgtggcta     1860
tgctggcccc tttgcctgtt cccgacaccc cagaaggtgt cgagatcatc ttttcgatct     1920
acccgatgaa cgagtcagcc cgggccacag atgactggtg caccttcaga gttatctccc     1980
```

```
atgaaggggt tgaaaattct tggattgagc actgcgttgg ttcagttcgt atagaaacgg    2040
gagagcagag gatatccgcc cctcctgttg acagccagtt gtcaatatgt tctgaagccg    2100
tcgatataaa ccaaatgtat cgagacttcg cctctgcggg aatggaattt ggcgacttcc    2160
tgaaaaacat tcgaagcat                                                 2179
```

<210> SEQ ID NO 8
<211> LENGTH: 314
<212> TYPE: DNA
<213> ORGANISM: Penicillium verrucosum
<220> FEATURE:
<221> NAME/KEY: misc_feature
<222> LOCATION: (265)..(265)
<223> OTHER INFORMATION: n is a, c, g, or t

<400> SEQUENCE: 8

```
gaattcacta gtgattgcga atgggtatgc gcggggcgaa gccattggct gtctaatact     60
caagccattg aagaatgctg ttcgagatgg ggatcatatt tacgctatca tccgaggatc    120
agggtctaac caggacggga gaaccccgg aatcacgctc cctagtgagg tggcgcaaga    180
ggctttgata cgacgcgtat atcaaatggc atgtcttaat ccagcagata ccgacttcgt    240
tgaggcctac ggcaccggca caatngaatt cccgcgagcc gccaggcggc cgggagctgg    300
aactcgggcc catg                                                      314
```

<210> SEQ ID NO 9
<211> LENGTH: 311
<212> TYPE: DNA
<213> ORGANISM: Penicillium verrucosum

<400> SEQUENCE: 9

```
catgggcccg agttcctgct cccggccgcc tggcggccgc gggaattcca ttgaatgggt     60
atgcgcgggg cgaggcagct ggctgtctta tccttaaacc cctagccaag gcgttgcacg    120
accgggacaa catcagggcc gtaatacgag gaaccggttc caatcaagac gggcgcaccg    180
cagggataac actaccaaat ggggcagccc aagaaacctt gattcggagc gtctatacac    240
gggctggtct ggatccctcc gaaacagatt ttgtggaggc ctacggcacc ggcacaatca    300
ctagtgaatt c                                                         311
```

<210> SEQ ID NO 10
<211> LENGTH: 23
<212> TYPE: DNA
<213> ORGANISM: artificial sequence
<220> FEATURE:
<223> OTHER INFORMATION: synthesized primer

<400> SEQUENCE: 10

```
tatccgccgc ctcgcaaact aat                                             23
```

<210> SEQ ID NO 11
<211> LENGTH: 23
<212> TYPE: DNA
<213> ORGANISM: artificial sequence
<220> FEATURE:
<223> OTHER INFORMATION: synthesized primer

<400> SEQUENCE: 11

```
cgaccgatca tgcgaccgta aat                                             23
```

<210> SEQ ID NO 12

```
<211> LENGTH: 21
<212> TYPE: DNA
<213> ORGANISM: artificial sequence
<220> FEATURE:
<223> OTHER INFORMATION: synthesized primer

<400> SEQUENCE: 12
ctcggtgaca tcagggtat c                                              21

<210> SEQ ID NO 13
<211> LENGTH: 24
<212> TYPE: DNA
<213> ORGANISM: artificial sequence
<220> FEATURE:
<223> OTHER INFORMATION: synthesized primer

<400> SEQUENCE: 13
agcgtattca gtcactcatt caga                                          24

<210> SEQ ID NO 14
<211> LENGTH: 19
<212> TYPE: DNA
<213> ORGANISM: artificial sequence
<220> FEATURE:
<223> OTHER INFORMATION: synthesized primer

<400> SEQUENCE: 14
gctatgcgcg gagaagtca                                                19

<210> SEQ ID NO 15
<211> LENGTH: 21
<212> TYPE: DNA
<213> ORGANISM: artificial sequence
<220> FEATURE:
<223> OTHER INFORMATION: synthesized primer

<400> SEQUENCE: 15
aaggctgggg atcgtggagt g                                             21

<210> SEQ ID NO 16
<211> LENGTH: 19
<212> TYPE: DNA
<213> ORGANISM: artificial sequence
<220> FEATURE:
<223> OTHER INFORMATION: synthesized primer

<400> SEQUENCE: 16
agtttaccgg ccttgttga                                                19

<210> SEQ ID NO 17
<211> LENGTH: 24
<212> TYPE: DNA
<213> ORGANISM: artificial sequence
<220> FEATURE:
<223> OTHER INFORMATION: synthesized primer

<400> SEQUENCE: 17
ttattaccgt tgtcgctct tctc                                           24

<210> SEQ ID NO 18
<211> LENGTH: 24
<212> TYPE: DNA
<213> ORGANISM: artificial sequence
<220> FEATURE:
<223> OTHER INFORMATION: synthesized primer

<400> SEQUENCE: 18
```

```
agaacgggat gccaaaacag tgag                                              24

<210> SEQ ID NO 19
<211> LENGTH: 24
<212> TYPE: DNA
<213> ORGANISM: artificial sequence
<220> FEATURE:
<223> OTHER INFORMATION: synthesized primer

<400> SEQUENCE: 19
aagaatgcga gggatgggat aacc                                              24

<210> SEQ ID NO 20
<211> LENGTH: 26
<212> TYPE: DNA
<213> ORGANISM: artificial sequence
<220> FEATURE:
<223> OTHER INFORMATION: synthesized primer

<400> SEQUENCE: 20
ttctctactg cgcttctcac atccat                                            26

<210> SEQ ID NO 21
<211> LENGTH: 26
<212> TYPE: DNA
<213> ORGANISM: artificial sequence
<220> FEATURE:
<223> OTHER INFORMATION: synthesized primer

<400> SEQUENCE: 21
aacatcatag ccataagagg tcaaca                                            26

<210> SEQ ID NO 22
<211> LENGTH: 20
<212> TYPE: DNA
<213> ORGANISM: artificial sequence
<220> FEATURE:
<223> OTHER INFORMATION: synthesized pimer

<400> SEQUENCE: 22
agccgtgttt tcattctttc                                                   20

<210> SEQ ID NO 23
<211> LENGTH: 17
<212> TYPE: DNA
<213> ORGANISM: artificial sequence
<220> FEATURE:
<223> OTHER INFORMATION: synthesized primer

<400> SEQUENCE: 23
tgcggccatc ttcgtgt                                                      17

<210> SEQ ID NO 24
<211> LENGTH: 20
<212> TYPE: DNA
<213> ORGANISM: artificial sequence
<220> FEATURE:
<223> OTHER INFORMATION: synthesized primer
<220> FEATURE:
<221> NAME/KEY: misc_feature
<222> LOCATION: (3)..(3)
<223> OTHER INFORMATION: n is i
<220> FEATURE:
<221> NAME/KEY: misc_feature
<222> LOCATION: (9)..(9)
<223> OTHER INFORMATION: n is i
<220> FEATURE:
```

```
<221> NAME/KEY: misc_feature
<222> LOCATION: (15)..(15)
<223> OTHER INFORMATION: n is i
<220> FEATURE:
<221> NAME/KEY: misc_feature
<222> LOCATION: (18)..(18)
<223> OTHER INFORMATION: n is i

<400> SEQUENCE: 24
gcnaayggnt aygcnmgngg                                                   20

<210> SEQ ID NO 25
<211> LENGTH: 20
<212> TYPE: DNA
<213> ORGANISM: artificial sequence
<220> FEATURE:
<223> OTHER INFORMATION: synthesized primer
<220> FEATURE:
<221> NAME/KEY: misc_feature
<222> LOCATION: (3)..(3)
<223> OTHER INFORMATION: n is i
<220> FEATURE:
<221> NAME/KEY: misc_feature
<222> LOCATION: (6)..(6)
<223> OTHER INFORMATION: n is i
<220> FEATURE:
<221> NAME/KEY: misc_feature
<222> LOCATION: (9)..(9)
<223> OTHER INFORMATION: n is i
<220> FEATURE:
<221> NAME/KEY: misc_feature
<222> LOCATION: (15)..(15)
<223> OTHER INFORMATION: n is i

<400> SEQUENCE: 25
gtnccngtnc crtangcytc                                                   20

<210> SEQ ID NO 26
<211> LENGTH: 24
<212> TYPE: DNA
<213> ORGANISM: artificial sequence
<220> FEATURE:
<223> OTHER INFORMATION: synthesized primer

<400> SEQUENCE: 26
tgggtatgcg cggggtgagg gtat                                              24

<210> SEQ ID NO 27
<211> LENGTH: 24
<212> TYPE: DNA
<213> ORGANISM: artificial sequence
<220> FEATURE:
<223> OTHER INFORMATION: synthesized primer

<400> SEQUENCE: 27
ccgtaggctt cgaaaaactg acac                                              24

<210> SEQ ID NO 28
<211> LENGTH: 21
<212> TYPE: DNA
<213> ORGANISM: artificial sequence
<220> FEATURE:
<223> OTHER INFORMATION: synthesized primer

<400> SEQUENCE: 28
tgcacgaccg ggacaacatc a                                                 21

<210> SEQ ID NO 29
<211> LENGTH: 22
```

```
<212> TYPE: DNA
<213> ORGANISM: artificial sequence
<220> FEATURE:
<223> OTHER INFORMATION: synthesized primer

<400> SEQUENCE: 29
ccgtaggcct ccacaaaatc tg                                              22
```

US 7,560,234 B2

DETECTION OF OCHRATOXIN A PRODUCING FUNGI

This is a continuation of PCT/IE2004/000020 filed 12 Feb. 2004 and published in English.

INTRODUCTION

The invention relates to genes expressed by fungal cells producing the mycotoxin ochratoxin A (OTA) and a method for detecting ochratoxin A, particularly in food and feedstuffs.

BACKGROUND

Mycotoxins are a group of secondary metabolites which are produced by various filamentous fungi that can cause a toxic response termed a mycotoxicosis, if ingested by higher vertebrates and other animals.

Ochratoxin A (OTA) is a mycotoxin produced by *Aspergillus* and *Penicillium* species considered detrimental to human health and is classified as a possible human carcinogen. The recommended level for OTA in food for human consumption is 5 pg/kg for raw grain, 3 pg/kg for derived cereal products and 10 ilg/kg for dried vine fruits. The European Commission's Scientific Committee on Food has concluded that the intake of OTA should be reduced as far as possible to approximately 5 ng per kilogram of body weight per day (Scientific Committee for food 1996).

Cereals normally correspond to 50 to 80% of average consumer intake. OTA is found mainly in wheat and barley (Kuiper-Goodman 1996; Pittet 1998). It is also found in coffee (Burdaspal and Legarda, 1998; Dietrich et al., 1995, Jorgenson, 1998), wine (Burdaspal and Legarda, 1999; Visconti et al., 1999; Zimmerli and Dick, 1996), beer (Visconti et al., 2000), pork (Jorgenson, 1998; Wolff et al, 2000) and grapes.

Conventional methods for fungal detection and identification in a sample involve plating, incubation and identification based on morphological characteristics. These methods are time-consuming, labour intensive and require experienced personnel that may be lacking in many laboratories to interpret the results.

There is therefore a clear need for a more accessible and improved method for the detection and identification of the presence of OTA producing fungi present at even very low levels in a sample.

STATEMENTS OF INVENTION

According to the invention there is provided use of a gene which is expressed by fungal cells producing ochratoxin A, or a fragment, derivative, mutant or variant of the gene in the detection and/or identification of ochratoxigenic fungi.

The invention also provides use of a gene which is upregulated during ochratoxin A biosynthesis, or a fragment, derivative, mutant or variant of the gene in the detection and/or identification of ochratoxigenic fungi.

The invention further provides use of a protein having an amino acid sequence derived from any one or more of SEQ ID No 1, SEQ ID No 2, SEQ ID No 3, SEQ ID No 4, SEQ ID No 5, SEQ ID No 6 or SEQ ID No 7 or SEQ ID No 8 or SEQ ID No 9 in the detection and/or identification of an ochratoxin A producing fungi. The use may be in the detection and/or identification of fungi that express ochratoxin A biosynthetic genes.

In one aspect the invention provides use of a nucleotide sequence, gene, peptide or polypeptide or a fragment, derivative, or variant thereof having a nucleotide or amino acid sequence selected from any one or more of SEQ ID No. 1 or SEQ ID No. 2 or SEQ ID No. 3 or SEQ ID No. 4 or SEQ ID No. 5 or SEQ ID No. 6 or SEQ ID No. 7 or SEQ ID No 8 or SEQ ID No 9 in the detection and/or identification of an ochratoxigenic fungus.

The invention also provides use of a nucleotide sequence, gene, peptide or polypeptide or a fragment, derivative, or variant thereof having a nucleotide or amino acid sequence selected from any one or more of SEQ ID No. 1 or SEQ ID No. 2 or SEQ ID No. 3 or SEQ ID No. 4 or SEQ ID No. 5 or SEQ ID No. 6 or SEQ ID No. 7 or SEQ ID No. 8 or SEQ ID No. 9 in the construction of an atoxigenic strain of an ochratoxigenic fungus.

The ochratoxigenic fungus may be of the genus *Aspergillus*. The fungus may be of the species *carbonarius, niger, alliaceus* or *foetidus*.

Alternatively the ochratoxigenic fungus is of the genus *Penicillium*. The fungus may be of the species *verrucosum*.

The invention also provides:

An isolated nucleotide having SEQ ID No 1.

An isolated nucleotide having SEQ ID No 2.

An isolated nucleotide having SEQ ID No 3.

An isolated nucleotide having SEQ ID No 4.

An isolated nucleotide having SEQ ID No 5.

An isolated nucleotide having SEQ ID No 6.

An isolated nucleotide having SEQ ID No 7.

An isolated nucleotide having SEQ ID No 8.

An isolated nucleotide having SEQ ID No 9.

The invention also provides Oligonucleotide primers derived from any of these isolated nucleotides.

More particularly the invention provides PCR primers prepared derived from any of these isolated nucleotides.

The invention also provides an oligonucleotide primer selected from one or more of:

| SEQ ID No. | Primer | | Parent SEQ ID No. | Nucleotide Position in Parent Sequence |
|---|---|---|---|---|
| 10 | AOB02-F: | 5'-tatccgccgcctcgcaaactaat-3' | SEQ ID No. 6 | |
| 11 | AOB02-R: | 5'-cgaccgatcatgcgaccgtaat-3' | SEQ ID No. 6 | |
| 12 | AOB03-R: | 5'-ctcggtgacatcaggggtatc-3' | SEQ ID No. 5 | 949-969 |

-continued

| SEQ ID No. | Primer | | Parent SEQ ID No. | Nucleotide Position in Parent Sequence |
|---|---|---|---|---|
| 13 | AOB03-R: | 5'-agcgtattcagtcactcattcaga-3' | SEQ ID No. 5 | |
| 14 | AOE04-F: | 5'-gctatgcgcggagaagtca-3' | SEQ ID No. 2 | 804-822 |
| 15 | AOE04-R: | 5'-aaggctggggatcgtggagtg-3' | SEQ ID No. 2 | 1605-1085 |
| 16 | AOD07-F: | 5'-agtttaccggccttgttga-3' | SEQ ID No. 4 | |
| 17 | AOD07-R: | 5'-ttattaccgtttgtcgctcttctc-3' | SEQ ID No. 4 | |
| 18 | AOH11-F: | 5'-agaacgggatgccaaaacagtgag-3' | SEQ ID No. 1 | |
| 19 | AOH11-R: | 5'-aagaatgcgagggatgggataacc-3' | SEQ ID No. 1 | |
| 20 | 2B11-BF: | 5'-ttctctactgcgcttctcacatccat-3' | SEQ ID No. 7 | 2755-2780 |
| 21 | 2B11-BR: | 5'-aacatcatagccataagaggtcaaca-3' | SEQ ID No. 7 | 2963-2988 |
| 22 | PKS4-GAPF: | 5'-agccgtgttttcattctttc-3' | SEQ ID No. 7 | 1610-1629 |
| 23 | PKS4-GAPR: | 5'-tgcggccatcttcgtgt-3' | SEQ ID No. 7 | 2346-2362 |
| 24 | KS-DPA: | 5'-GCIAAYGGITAYGCIMGIGG-3' | SEQ ID No. 8 | |
| 25 | KS-DPB- | 5'-GTICCIGTICCRTAIGCYTC-3' | SEQ ID No. 8 | |
| 26 | ACKS-1F: | 5'-tgggtatgcgcggggtgagggtat-3' | SEQ ID No. 8 | |
| 27 | ACKS-1R: | 5'-ccgtaggcttcgaaaaactgacac-3' | SEQ ID No. 8 | |

The invention further provides an Oligonucleotide primer selected from one or more of:

| SEQ ID No. | Primer | | Parent SEQ ID No. |
|---|---|---|---|
| 24 | KS-DPA: | 5'-GCIAAYGGITAYGCIMGIGG-3' | SEQ ID No. 9 |
| 25 | KS-DPB- | 5'-GTICCIGTICCRTAIGCYTC-3' | SEQ ID No. 9 |
| 28 | PVKS-1F: | 5'-tgcacgaccgggacaacatca-3' | SEQ ID No. 9 |
| 29 | PVKS-1R: | 5'-ccgtaggcctccacaaaatctg-3' | SEQ ID No. 9 |

In another aspect the invention provides an assay for the detection of ochratoxin A producing fungi comprising a nucleotide sequence, gene, peptide or polypeptide or a fragment, derivative, or variant thereof having a nucleotide or amino acid sequence selected from any one or more of SEQ ID No. 1 or SEQ ID No. 2 or SEQ ID No. 3 or SEQ ID No. 4 or SEQ ID No. 5 or SEQ ID No. 6 or SEQ ID No. 7 or SEQ ID No 8 or SEQ ID No 9.

The invention also provides an assay for the detection and identification of ochratoxin A producing genes comprising a nucleotide sequence, gene, peptide or polypeptide or a fragment, derivative, or variant thereof having a nucleotide or amino acid sequence selected from any one or more of SEQ ID No. 1 or SEQ ID No. 2 or SEQ ID No. 3 or SEQ ID No. 4 or SEQ ID No. 5 or SEQ ID No. 6 or SEQ ID No. 7 or SEQ ID No 8 or SEQ ID No 9.

In a further aspect the invention provides an atoxigenic strain of the genus *Aspergillus*. The atoxigenic strain may be of the species *ochraceus, carbonarius, alliaceus, foetidus* or *niger*.

In another aspect the invention provides an atoxigenic strain of the genus *Penicillium*. The atoxigenic strain may be of the species verrucosum.

The atoxigenic strain may comprise a nucleotide sequence, gene, peptide or polypeptide or a fragment, derivative, or variant thereof having a nucleotide or amino acid sequence selected from any one or more of SEQ ID No. 1 or SEQ ID No. 2 or SEQ ID No. 3 or SEQ ID No. 4 or SEQ ID No. 5 or SEQ ID No. 6 or SEQ ID No. 7 or SEQ ID No 8 or SEQ ID No 9.

The invention further provides use of a nucleotide sequence, gene, peptide or polypeptide or a fragment, derivative, or variant thereof having a nucleotide or amino acid sequence selected from any one or more of SEQ ID No. 1 or SEQ ID No. 2 or SEQ ID No. 3 or SEQ ID No. 4 or SEQ ID No. 5 or SEQ ID No. 6 or SEQ ID No. 7 or SEQ ID No. 8 or SEQ ID No. 9 to identify or isolate a nucleotide sequence, gene, peptide or polypeptide involved in ochratoxin A biosynthesis. The sequences may be used for so-called chromosome walking or gene library screening experiments to obtain other DNA sequences contiguous to the sequences involved in OTA production.

BRIEF DESCRIPTION OF THE DRAWINGS

The invention will be more clearly understood from the following descriptions thereof, given by way of example only, with reference to the accompanying drawings, in which: —

FIG. 6 Shows RT-PCR analysis expression of the pAs gene in *Aspergillus foetidus* ATCC 10254, using the 2B11 primer pair (SEQ ID No. 20 and 21). During growth on (1) malt extract broth, (2) potato dextrose broth and (3) yeast extract glucose broth. Lanes 1, 2 and 3 are G3PDH controls. Lanes 1', 2' and 3' are the 2B11 primer reactions. +VE is positive control, -VE are negative controls.

FIG. 7 Shows production of OTA by *A. foetidus* ATCC10254 mycelium from which the RNA for the above RT-PCR experiment was extracted.

FIG. 8 Shows RT-PCR measurement of expression of the pks gene by *Aspergillus niger* ATCC9029 using the GAP primer pair (SEQ ID No. 22 and 23). During growth on (1) malt extract broth, (2) potato dextrose broth and (3) yeast extract glucose broth. Lanes 1, 2 and 3 are G3PDH controls. Lanes 1', 2' and 3' are the 2B11 primer reactions. +VE is positive control, -VE are negative controls.

DETAILED DESCRIPTION

Figure 1:
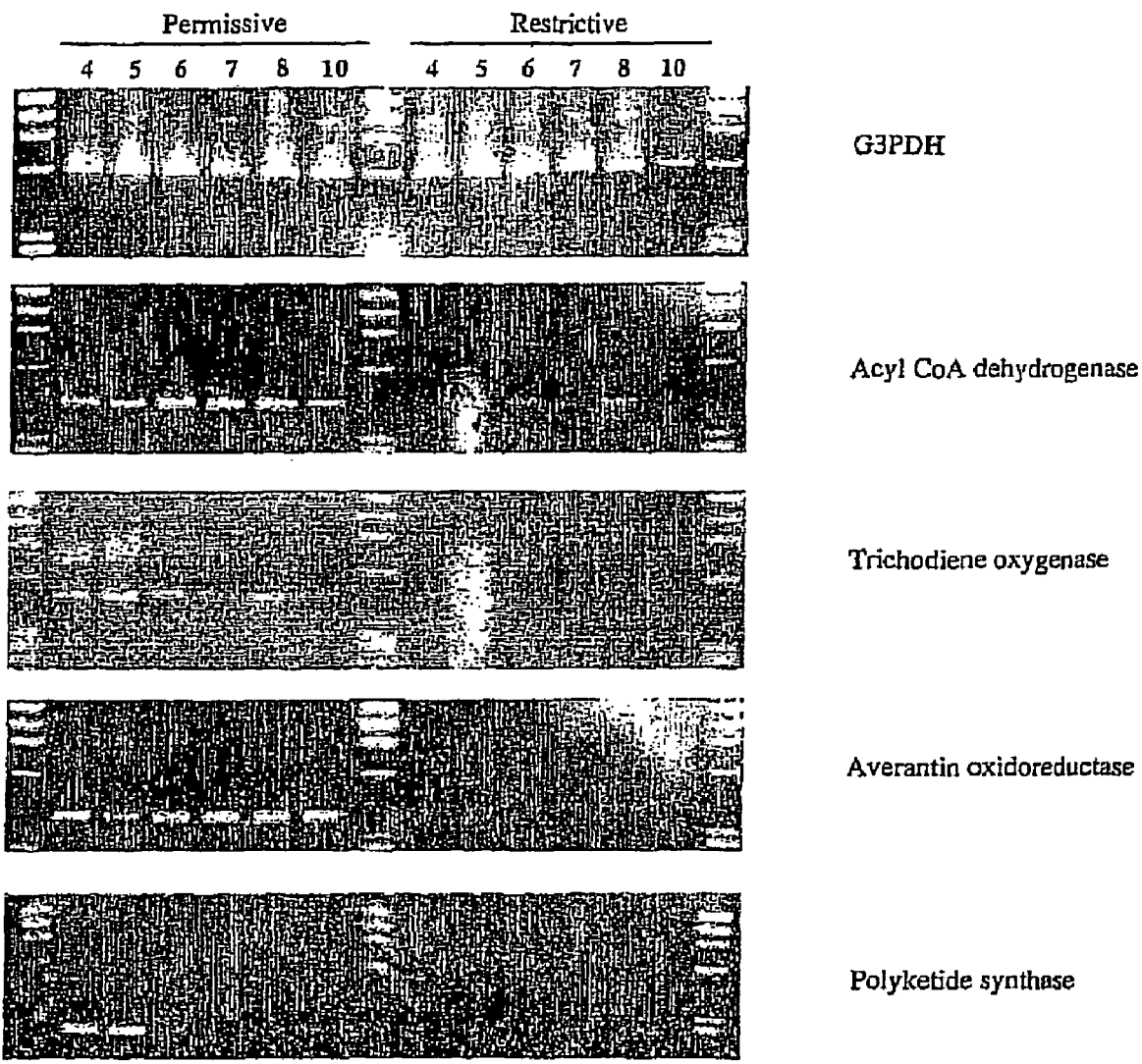
FIGS. 1 (a) to (e) show the results of RT-PCR on the expression of cloned genes during OTA production by *Aspergillus ochraceus* HP99. Expression of Glyceraldehyde-3-phosphate dehydrogenase (G3PDH) (a) is used as a control. Samples were taken at 4, 5, 6, 7, 8 and 10 day time intervals.

The invention provides isolated nucleotide sequences and genes expressed by fungal cells producing OTA and believed to be involved in the biosynthetic pathway for OTA biosynthesis.

The invention also provides detection methods based on these isolated nucleotide sequences to detect the presence of fungi producing OTA in a sample.

The detection methods of the invention provide simple and more rapid assays for the detection of ochratoxigenic fungi and have significant advantages over the detection methods currently available.

To date the biosynthetic pathway for OTA biosynthesis has not been characterised. However, the cloning and characterisation of the genes of the invention greatly increases the understanding of the biosynthetic pathway. The cloning and molecular characterisation of mycotoxin biosynthetic genes is vital in order to gain a fuller understanding of the organisation, regulation and expression of these genes.

In the invention suppression substractive hybridisation PCR (SSH-PCR) was used to clone a pool of cDNA sequences from *Aspergillus ochraceus* HP99 (University College Cork, Dept. of Microbiology, Culture Collection) that are expressed at higher levels during OTA biosynthesis. The cloned DNA sequences were then compared to sequences deposited in various databases in order to identify putative OTA biosynthetic genes.

A number of novel cloned DNA sequences were found to be expressed only by fungal cells producing OTA.

Polymerase chain reaction (PCR) based detection methods have the potential to detect and identify the present of mycotoxigenic fungi present at very low levels.

(Geisen, 1998; Edwards et al., 2002).

Using the novel DNA sequences of the invention oligonucleotide primer pairs of the identified sequences were prepared. The oligonucleotide primer pairs form the basis of two nucleic acid based detection methods of the invention.

The detection methods of the invention use PCR and are extremely specific to the particular genus/species. They provide rapid detection using techniques which are easily learnt. The methods are based on the identification and isolation of the novel gene sequences of the invention which have been found to be specific to OTA.

In the first method a conventional PCR assay is used to detect fungi that have the capacity to produce OTA by indicating the presence of OTA biosynthesis genes in fungal isolates. DNA from fungal isolates may be used as a template in PCR reactions. Oligonucleotide primers derived from the cloned gene sequences detect fungal isolates that are capable of producing OTA. Modern Real-time PCR based protocols can provide results in less than 40 minutes.

In the second method a reverse transcription (RT)-PCR based assay is used to identify fungi that are expressing the OTA biosynthetic genes and are therefore toxigenic. The RT-PCR assay detects the level of transcription (production of messenger RNA, mRNA) for a specific gene. The assay is performed in two stages (1) synthesis of cDNA from mRNA and (2) amplification of specific target sequences by PCR. The RT-PCR based assay provides highly specific detection of mRNA transcripts from the targeted genes. As RNA synthesis is the primary step in producing the enzymes necessary for any biosynthetic pathway the highly sensitive PCR based method demonstrates toxigenicity even when the amount of toxin produced is not detectable by conventional assays.

The isolation of the genes of the invention therefore has significant commercial benefit. The isolated DNA sequences may be used in a variety of assays for the detection of fungi producing ochratoxin A.

The PCR based detection system will detect the producing organism thereby allowing identification of potential problems from mycotoxin contamination prior to any significant amounts of toxin being produced.

A potential market for assays which can detect even the smallest amount of OTA producing fungi are the brewing, baking, wine making or animal feed industries as well as coffee manufacturers and cereal producers. The detection of OTA producing fungi or the presence of genes producing OTA at an early stage would ensure that the contaminated produce does not enter the food chain at source. Positive detection would lead to disposal of the contaminated produce and/or treatment to remove it.

The identification and isolation of the genes involved in the biosynthesis of OTA has valuable therapeutic potential. Mycotoxins are known to be involved in a number of disease states including cancer of the liver, damage of kidneys, weakening of the immune system, allergic reactions, ergotism and poisoning. Easy to use and rapid PCR based methods by which OTA producing fungi may be detected in source samples is therefore highly desirable.

The identification and characterisation of OTA producing genes is also important in determining the conditions under which the fungus produces the mycotoxin. The RT-PCR assay allows identification of the physiological parameters that promote ochratoxin production during storage such as water activity, temperature, pH etc. Storage conditions that are unfavourable to ochratoxin production can then be used to reduce or eliminate ochratoxin production in stored products. Information on the conditions that inhibit ochratoxin production are also essential to the use of HACCP to ensure mycotoxin-free food and animal feed.

The genes of the invention may also be used in the construction of atoxigenic strains of *A. ochraceus, A. carbonarius, A. alliaceus, A. niger, A. foetidus*, or *Penicillium verrucosum*. Atoxigenic strains are strains which are genetically engineered not to produce OTA. These strains may therefore be used in biocontrol strategies for the elimination of OTA production. In this way atoxigenic stains of fungi may be used without the risk of OTA being produced.

The genes of the invention may also be used to determine whether strains of *Aspergillus* strains which are used in industrial fermentations possess ochratoxin A biosynthetic genes i.e. the ability to produce the mycotoxin.

The genes of the invention may also be used to monitor whether OTA is being produced in industrial fermentations involving *Aspergillus* strains.

The invention will be more clearly understood from the following examples.

Methodology

The method of SSH-PCR used is described in detail by Diatchenko et al. (1996) and a commercially available kit for the procedure is produced by Clontech laboratories (Palo Alto, Calif., USA).

(1) Development of Permissive and Restrictive Growth Media

The growth conditions under which *Aspergillus ochraceus* HP99 produced OTA (permissive) and did not produce OTA (restrictive) were identified. A number of different growth media were examined and it was observed that OTA was not produced when *A. ochraceus* was grown on Potato dextrose medium (PD) or malt extract medium (ME) either as liquid medium or solid medium. High levels of OTA production were observed if *A. ochraceus* was grown on yeast extract sucrose (YES) or Czapek-Dox medium containing yeast extract and casamino acids (MC).

(2) SSH-PCR Procedure

Total ribonucleic acid (RNA) was isolated from *A. ochraceus* HP99 mycelia grown on permissive (MC) and restrictive (PD) media. Double stranded complementary DNA (cDNA) was then synthesised from each RNA preparation using a SMART™ cDNA synthesis kit (Clontech Laboratories, Palo Alto, Calif., USA) and used to perform a suppression-subtractive hybridisation-PCR experiment (SSH-PCR) experiment. The success of the subtractive hybridisation in eliminating DNA sequences common to both samples was determined by quantitative PCR on the SSH-PCR product using primers to the constitutively expressed housekeeping gene glyceraldehyde-3-phosphate dehydrogenase (G3PDH). The G3PDH gene was detectable at 5-10 fewer PCR cycles in the control sample, demonstrating a reduction in abundance of between $2^5$ and $2^{10}$ fold in the subtracted sample.

(3) Cloning Screening and Sequencing of SSH-PCR Products.

The PCR products resulting from the SSH-PCR were ligated into the pGEM-T easy vector (Promega Laboratories, Madison, Wis., USA) and the ligations transformed into *Escherichia coli* TOP 10 competent cells (Invitrogen). A large number of transformants were obtained and 1,440 were replica plated onto 155 mm LB agar plates.

To screen the replica plated clones for increased expression during OTA production a portion of each colony was picked and emulsified in 100, 1 of sterile water, zip of each colony suspension was then used as a template in a PCR reaction using the PCR primers used to amplify the final SSH-PCR products. The PCR products obtained from this procedure were spotted onto duplicate nitrocellulose membranes (2. 5. 1 per spot) and the DNA was fixed to the membranes by ultraviolet (UV) transillumination. The prepared membranes were then used in a hybridisation experiment to identify up-regulated clones. One membrane from each pair was probed with $^{32}$P-ATP labelled cDNA from a permissive *A. ochraceus* culture and the other with $^{32}$P-ATP labelled cDNA from a restrictive culture. Up-regulated clones were taken to be those for which the PCR product hybridised to the permissive probe but not to the restrictive probe. Clones that hybridised to both probes were disregarded. A total of 500 were screened of which 230 (46%) were upregulated (i.e. hybridised to permissive cDNA but not to restrictive cDNA). 192 up-regulated clones were selected for DNA sequencing. The nucleotide sequence of the cloned DNAs was determined and the deduced amino acid sequence of each sequence was compared to the protein sequence databases using the BLAST-X algorithm. The BLAST-X search translated the sequences in all 6 possible reading frames and compared them to the protein sequence databases (Table 1). 83 (55%) of the sequences were identifiable following the BLAST-X search. The largest number of identifiable clones encoded proteins with a role in cell metabolism, in addition about 30% of the sequences were classed as miscellaneous in that they could not be assigned to any of the several groupings. A number of clones with a potential role in ochratoxin biosynthesis were selected for further study. The nucleotide sequences of the selected clones are given in SEQ ID NO: 1-9.

(4) Further Studies on the Cloned Sequences

The presence of the cloned sequences in the genomic DNA of *A. ochraceus* and *A. carbonarius* 23804 was demonstrated by PCR using primers designed to the cloned sequences.

Reverse transcription-PCR was used to measure the expression of each of the cloned genes during OTA production.

TABLE 1

| BLASTX hit | size of clone (bp) |
|---|---|
| Averantin oxidoreductase | 630 |
| HC toxin synthase | 371 |
| Regulatory gene | 666 |
| 3-oxoacyl synthase | 846 |
| Trichodiene oxygenase | 572 |
| Acyl CoA dehydrogenase | 670 |
| Polyketide synthase | 408 |

The most significant appears to be a gene encoding a protein sequence similar to a number of polyketide synthase (PKS) proteins. As the ochratoxin A molecule contains a polyketide structure a polyketide synthase gene is essential for its biosynthesis. The presence of all of the genes in the *A. ochraceus* genome was confirmed by PCR with primers designed to each of the cloned sequences. Most of the PCR primer pairs also amplified products of the correct size from the OTA producing fungus *Aspergillus carbonarius* 23804.

span an intron) from the genomic and cDNA respectively are in lanes 1 and 2 and are identical in size.

Primers Used:

| SEQ ID No. | Primer | Parent SEQ ID No. | Nucleotide Position In Parent Sequence |
|---|---|---|---|
| 20 | 2B11-BF: 5'-ttctctactgcgcttctcacatccat-3' | SEQ ID No. 7 | 2755-2780 |
| 21 | 2B11-BR: 5'-aacatcatagccataagaggtcaaca-3' | SEQ ID No. 7 | 2963-2988 |
| 30 | AOKSRT2-F: 5'-ctgacaccatcgaaaacctaaaaa-3' | SEQ ID No. 7 | 1800-1823 |
| 31 | AOKSRT2-R: 5'-tctaactcgcccttgacctg-3' | SEQ ID No. 7 | 2503-2522 |

To confirm that the genes were up-regulated during OTA biosynthesis the RNA was isolated at a number of time points [4, 5, 6, 7, 8, and 10 days] from *A. ochraceus* cultures growing on permissive and restrictive medium and used in a RT-PCR experiment to estimate the expression level for each clone.

Reverse transcription-PCR (RT-PCR) studies of the expression of 4 of the selected clones under growth conditions permissive and restrictive for OTA production was carried out.

Figure 2:
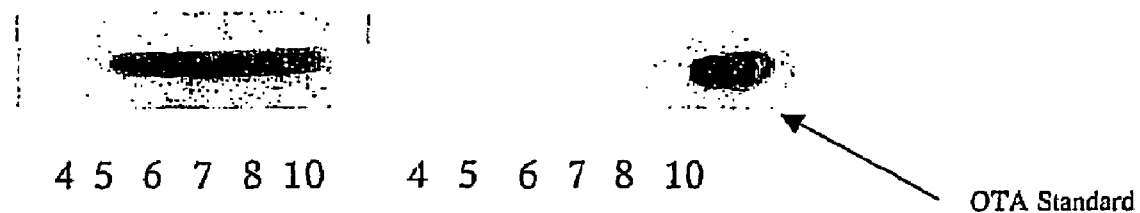
FIG. 2 shows the use of a PCR primer pair AOKS-RT2 (SEQ ID No. 30 and 31) to distinguish between genomic and cDNA. The 2B11 primer reactions are included for comparison.

Total RNA was extracted from *Aspergillus ochraceus* mycelium at different time-points during growth. cDNA was prepared from each RNA sample and used as a template in a PCR reaction with primers specific to each of the selected genes. Primers to the glyceraldehyde 3-phosphate dehydrogenase gene that is constitutively expressed were used in control reactions. OTA production was measured at each time point [4, 5, 6, 7, 8, and 10 days] by thin-layer chromatography to confirm that the growth conditions were permissive or restrictive as appropriate (FIG. 2).

The reverse transcription step produces DNA complementary to all RNA molecules in a particular sample thus the presence of a product in the subsequent PCR reaction is evidence that the RNA transcript for a specific gene was present at a particular time point.

The RT-PCR assay detects the level of transcription (production of mRNA) for a specific gene. RNA was isolated from fungal mycelia under permissive (OTA being produced) and restrictive (OTA not being produced) conditions. The RNA transcripts were reverse transcribed (complementary DNA (cDNA) molecules were synthesised) by the enzyme reverse transcriptase. The cDNA molecules were then detected by PCR. In the example no (or very low levels) transcripts from the OTA biosynthetic genes were detected when OTA was not being synthesised (FIG. 1).

As shown in FIG. 1 the glyceraldehyde-3-phosphate gene was expressed in all of the samples in both the permissive and restrictive cultures. The SSH-PCR clones were expressed strongly only in the permissive cultures. It was noticeable that the expression levels were highest at the earlier timepoints when it was most likely that OTA was being actively synthesised.

Figure 3:
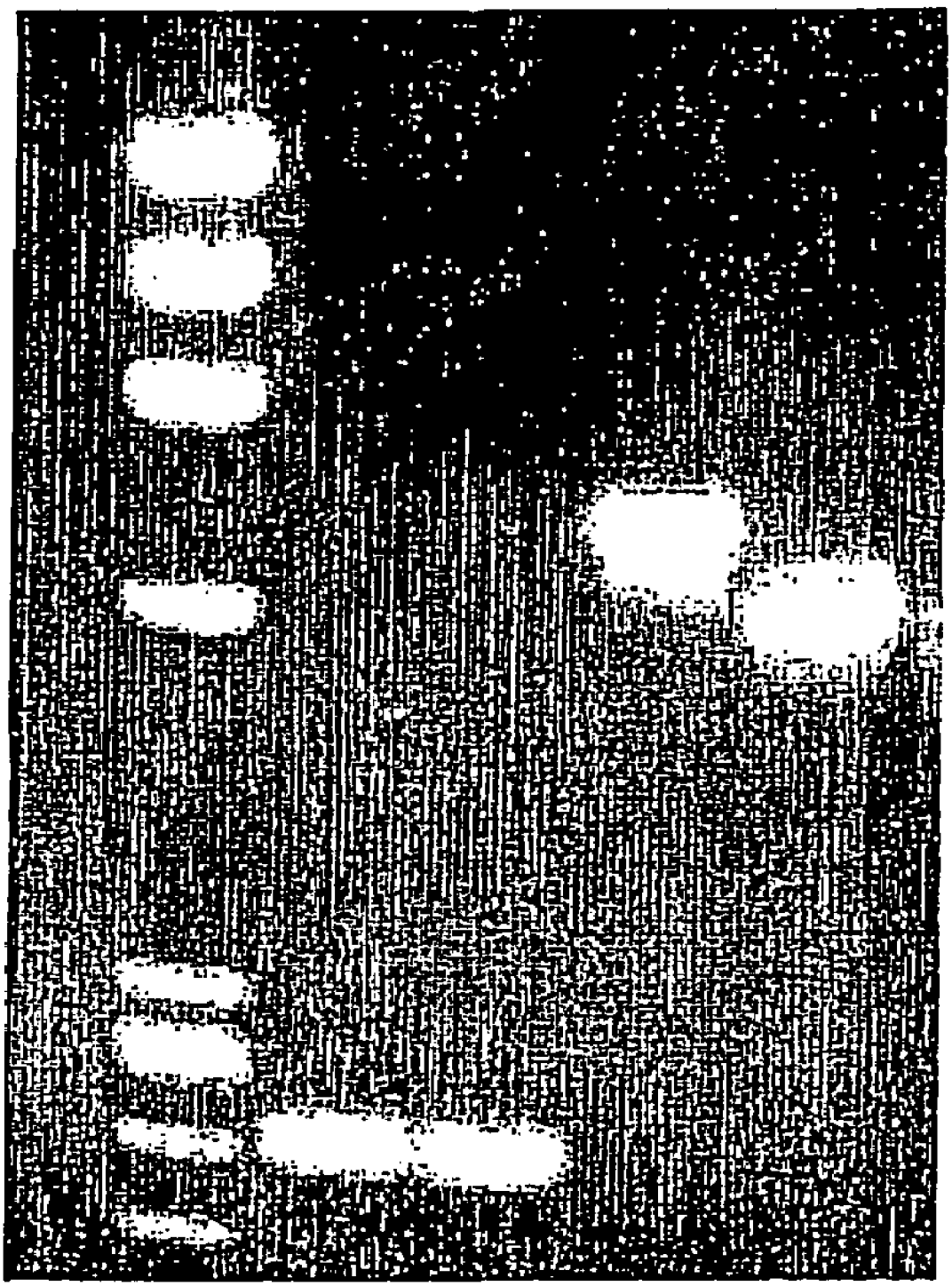
FIG. 3 shows the results of thin layer chromatography (TLC) at each time interval.

The use of an intron-spanning primer pair (AOKS-RT2) (SEQ ID No. 30 and 31) (FIG. 1 (*f*)) provides additional assurance that it is cDNA that has been detected rather than genomic DNA contamination. The intron is absent from cDNA having been spliced out of the RNA transcript. The genomic DNA product (lane 3) is therefore larger than that from cDNA (lane 4). The 2B11 primer products (that do not To confirm the involvement of the pks gene in OTA biosynthesis, a mutant of *A. ochraceus* [AO 118] was created which is incapable of producing ochratoxin A, through inactivation of the polyketide synthase (ks) gene. A hygromycin resistance gene cassette was inserted into the (pks) gene on the chromosome of *A. ochraceus*, so that the pks sequence was interrupted. Disruption of the pks gene was confirmed by the acquisition of hygromycin resistance by *A. ochraceus*. The hygromycin resistant transformants were then screened by plating on coconut cream agar (CA), OTA is fat soluble and therefore will diffuse into the fat present in the coconut cream. As OTA is fluorescent under UV light, exposure of the plates to UV allows identification of OTA producing strains by the presence of a blue fluorescent 'halo' around the culture, identified by the arrow in FIG. 3.

Figure 4:
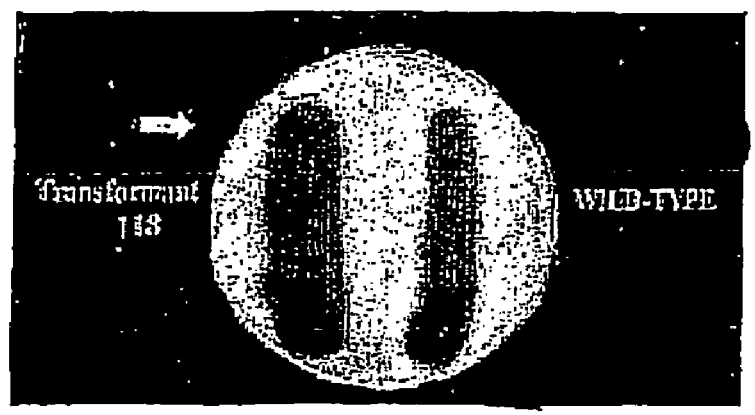
FIG. 4 shows the results of a plate screening confirming the involvement of the pks gene in OTA biosynthesis. The blue fluorescent halo is indicated by an arrow.
Figure 5:
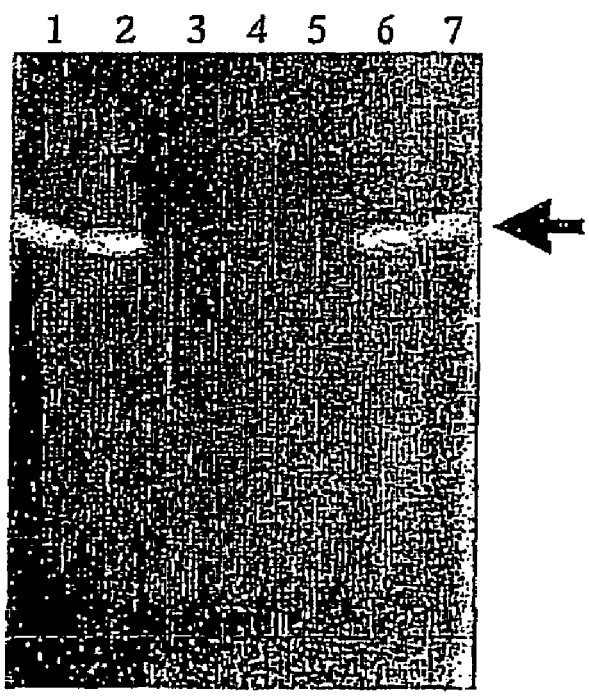
FIG. 5 shows the results of TLC on atoxigenic strains of *A. ochraceus* (AO118 [lane 5]; A0107 [lane 4]; A053 [lane 3]) in comparison to ochratoxin A standards (lanes 1 and 7) and wild type *A ochraceus* extract (lanes 2 and 6). The position of OTA is indicated by the arrow.

Transformants that appeared to be atoxigenic (OTA negative) after screening on CA were subjected to confirmatory testing by cutting out agar plugs from the medium and extracting the ochratoxin by treatment with acidified chloroform. The extracts [A0118, A0107 and A053] were run on thin layer chromatography (TLC) plates that were visualised under UV light (FIG. 4). From these tests it is clear that the pks gene [7. SEQ ID No. 7 (Polyketide synthase (2179 bp)] encodes a polyketide synthase gene which is essential for OTA production in *A. ochraceus*.

Isolation of pks Ketosynthase Regions from *Penicillium verrucosum* and *Aspergillus carbonarius*.

Genomic DNA was isolated from *Aspergillus carbonarius* 23804 and *Penicillium verrucosum* OTA11 and used as a template in PCR reactions with degenerate primers designed from the deduced protein sequence of the ketosynthase region (KS) of the *A. ochraceus* pks gene. The PCR reactions produced products of the correct size from both fungi. The PCR product was purified by elution from an agarose gel and ligated into the pGEM-T easy vector. The ligation mixture was transformed into Top 10F chemically competent *Escherichia coli* cells (Invitrogen) and the transformed cells were plated on LB agar containing Ampicillin (100 µg/ml), IPTG and X-GAL. A number of white colonies were selected and screened for the presence of the 2B11 PCR product by emulsifying a portion of the colony in 50 µl of distilled water and using 2 µl of the colony suspension as a template in a PCR reaction with the 2B11-B primer pair (SEQ ID No. 20 and 21). A transformant containing the correct PCR product was selected and grown in LB broth; plasmid DNA was prepared from the LB culture using the Qiagen Spin Mini-Prep plasmid DNA isolation kit. The DNA sequence of the cloned PCR product was determined by Lark Technologies Inc., Saffron Walden, Essex, United Kingdom. The nucleotide sequence was compared to existing nucleotide and protein databases using the BLAST and BLAST-X programs on the NCBI website. Both sequences showed strong homology to the KS region of PKS proteins from a number of fungi, including some known to be implicated in the biosynthesis of polyketide mycotoxins.

Primers Used

```
KS-DPA: 5'-GCIAAYGGITAYGCIMGIGG-3'  (SEQ ID No. 24)

KS-DPB-5'-GTICCIGTICCRTAIGCYTC-3'   (SEQ ID No. 25)
```

Referring to FIG. 8, no OTA was detected in the culture medium even though we have previously demonstrated OTA production by this strain. Measurement of the pks expression using the GAP primer pair in a RT-PCR assay showed that only a small amount of expression was occurring. This is in contrast to the higher level of pks expression observed in the *A. foetidus* strain that was producing OTA under these growth conditions (FIGS. 6 and 7).

The PCR primer pairs used for the RT-PCR assay were designed from the *A. ochraceus* pks DNA sequence. The data in FIGS. 6 and 8 demonstrates their application to the detection of OTA production in other *Aspergillus* species.

Cloning of a pks Homolog from *Aspergillus niger*.

Genomic DNA was isolated from *Aspergillus niger* 9029 and *Aspergillus foetius* 10254 and was used as a template in PCR reactions with two PCR primer pairs. The primer pair 2B11-B (SEQ ID No. 20 and 21) produced a product from *A. niger* and the PKS4-GAP primer pair (SEQ ID No. 22 and 23) produced a product from *A. foetidus*. The products were the same size as those produced by these primers in *A. ochraceus*.

The PCR products was purified by elution from an agarose gel and ligated into the pGEM-T easy vector. The ligation mixtures were transformed into Top 10F chemically competent *Escherichia coli* cells (Invitrogen) and the transformed cells were plated on LB agar containing Ampicillin (100 µg/ml), IPTG and X-GAL. A number of white colonies were selected and screened for the presence of the 2B11 (SEQ ID No. 20 and 21) PCR product by emulsifying a portion of the colony in 50 µl of distilled water and using 2 µl of the colony suspension as a template in a PCR reaction with the 2B11-B primer pair (SEQ ID No. 20 and 21). A transformant containing the correct PCR product was selected and grown in LB broth, plasmid DNA was prepared from the LB culture using the Qiagen Spin Mini-Prep plasmid DNA isolation kit. The DNA sequence of the cloned PCR product was determined by Lark Technologies Inc., Saffron Walden, Essex, United Kingdom. The nucleotide sequence was compared to existing nucleotide and protein databases using the BLAST and BLAST-X programs on the NCBI website.

Primers Used (all Specific to the pks Gene)

```
                                        (SEQ ID No. 20)
   2B11-BF: 5'-ttctctactgcgcttctcacatccat-3'

(SEQ ID No. 21)
   2B11-BR: 5'-aacatcatagccataagaggtcaaca-3'

(SEQ ID No. 22)
   PKS4-GAPF: 5'-agccgtgttttcattctttc-3'

(SEQ ID No. 23)
   PKS4-GAPR: 5'-tgcggccatcttcgtgt-3'
```

Primers Used for *Aspergillus*

| Primer | SEQ ID No. | Target gene. | Nucleotide Position In Target Gene |
|---|---|---|---|
| AOB02-F: 5'-tatccgccgcctcgcaaactaat-3' | 10 | SEQ ID No. 6 | |
| AOB02-R: 5'-cgaccgatcatgcgaccgtaaat-3' | 11 | SEQ ID No. 6 | |
| AOB03-R: 5'-ctcggtgacatcaggggtatc-3' | 12 | SEQ ID No. 5 | 949-969 |
| AOB03-R: 5'-agcgtattcagtcactcattcaga-3' | 13 | SEQ ID No. 5 | |
| AOE04-F: 5'-gctatgcgcggagaagtca-3' | 14 | SEQ ID No. 2 | 804-822 |
| AOE04-R: 5'-aaggctggggatcgtggagtg-3' | 15 | SEQ ID No. 2 | 1065-1085 |
| AOD07-F: 5'-agtttaccggccttgttga-3' | 16 | SEQ ID No. 4 | |
| AOD07-R: 5'-ttattaccgtttgtcgctcttctc-3' | 17 | SEQ ID No. 4 | |
| AOH11-F: 5'-agaacgggatgccaaaacagtgag-3' | 18 | SEQ ID No. 1 | |
| AOH11-R: 5'-aagaatgcgagggatgggataacc-3' | 19 | SEQ ID No. 1 | |
| 2B11-BF: 5'-ttctctactgcgcttctcacatccat-3' | 20 | SEQ ID No. 7 | 1610-1629 |
| 2B11-BR: 5'-aacatcatagccataagaggtcaaca-3' | 21 | SEQ ID No. 7 | 2963-2988 |
| PKS4-GAPF: 5'-agccgtgttttcattctttc-3' | 22 | SEQ ID No. 7 | 1610-1629 |
| PKS4-GAPR: 5'-tgcggccatcttcgtgt-3' | 23 | SEQ ID No. 7 | 2346-2362 |
| KS-DPA: 5'-GCIAAYGGITAYGCIMGIGG-3' | 24 | SEQ ID No. 8 | |
| KS-DPB-5'-GTICCIGTICCRTAIGCYTC-3' | 25 | SEQ ID No. 8 | |

| Primer | SEQ ID No. | Target gene. | Nucleotide Position In Target Gene |
|---|---|---|---|
| ACKS-1F: 5'-tgggtatgcgcggggtgagggtat-3' | 26 | SEQ ID No. 8 | |
| ACKS-1R: 5'-ccgtaggcttcgaaaaactgacac-3' | 27 | SEQ ID No. 8 | |

Primers Used for *Penicillium*

| Primer | SEQ ID No. | Target gene. |
|---|---|---|
| KS-DPA: 5'-GCIAAYGGITAYGCIMGIGG-3' | 24 | SEQ ID No. 9 |
| KS-DPB-5'-GTICCIGTICCRTAIGCYTC-3' | 25 | SEQ ID No. 9 |
| PVKS-1F: 5'-tgcacgaccgggacaacatca-3' | 28 | SEQ ID No. 9 |
| PVKS-1R: 5'-ccgtaggcctccacaaaatctg-3' | 29 | SEQ ID No. 9 |

Typical PCR Assays Utilising the Invention

The methodology for the PCR assays depends on whether the assay is to detect the presence of fungi that are capable of producing OTA by detecting a biosynthetic gene (PCR) or to detect production of OTA by measuring expression of the biosynthetic gene (RT-PCR).

For the PCR assay a sample such as a grain sample will be ground to break up the grains and DNA extracted from the ground grains using a Qiagen DNeasy plant mini-kit (Qiagen GmBH). The extracted DNA will be used as a template in a PCR reaction with one of the primer pairs listed above. Production of a PCR product of the correct size is taken as a positive result. The PCR assay can be performed on a real-time PCR apparatus such as a Light Cycler™ (Roche Molecular Biochemicals) and this will provide results within 1 hour. The total time from receipt of samples to production of results can be as short as 2-3 hours.

For the RT-PCR assay, a sample such as a grain sample will be ground in liquid nitrogen and the RNA extracted using a commercially available extraction kit such as the RNeasy™ (Qiagen GmBH). cDNA will then be prepared from the RNA by use of the reverse transcriptase enzyme. Once the cDNA has been prepared the procedure is identical to that for the PCR assay.

The invention is not limited to the embodiments hereinbefore described which may be varied in construction and detail.

APPENDIX 1

1. SEQ ID No. 1 (Averantin oxidoreductase (630bp))
GGCCGCGGGAATTCGATTGGCCGCCCGGGCAGGNACTTTTTTTTTTTTT
TTTTTTTCAATTTCAATCTGACCNTNTATTTGNGTGTAGTTGACAGTAAA
TCGGAGAATTAATTAAATACAAAATCAGGAGAACGGGATGCCAAAACAGT
GAGGCGAAAGAGTGAGGCGACACAACTCAAAACTGCCATCTCCGATTTGA
ATCGAACCAAGGAATAAATAATCACCTGCACCCAATTCACAGGAGCAAT
GTCACTCTGGGACCTATCCAGGACTGAAACAATAACTCAATAAATCGAT
GCTATCTCGTAGCTGCTTGCCCAGTTGGTCCATTCAAACCTGGCGAGTAG
ATCATCTAGGAAGCTTTAGGCGTANACTGTGAANAAGAGCGCGCGAGAC
AAGTGGTATAACGGGAATAAACACAACATTCCGCACATCCTTACCGATG
CACTGGAGTCAACTTCACCTTCAATGGATCCTTTTCCCAGATGTTGTAAG
ACTTTTGGTTATCCCATCCCTCGCATTCTTCTTCAAATGCCAGGTCAAAG
TTCCACAGTAGCTTCACGGCAATCAGACGCATTTCGGCATAAGCAAGATT
CCTTTCCGAGGCAGTTCCCTGGGCCCGTAGGAAA 2. SEQ ID No. 2 (HC Toxin synthase (371 bp))
ACCGCTATGCGCGGAGAAGTCAGCGTGGGCTATTGTCGNTTTTNTTGCGA
TTCTGAAAGCTGGAGCTGCCTGTACNCCNCTCGAGCCGTCTCATCCGCGA
GATAGATTGAAAAACTTGATTCGAGCCTGTGGTGCAACAGCCGTTGTGGT
AACGGCCCCACACGCCTCAATGCTTGAGATGGAGGGAATTGATGTCGTC
GTCGTTTCTTCCAAGACTGTATCGTCTCGGGATGAAGGTTTGGCTTGTGT
AGCCAATGCCACGGTCACTCCACGATCCCCAGCCTTTCTAATGTGGACAT
CTGGAAGCACGGGAAACCCCAAAGGCGTCGTTCTGGAACATGCAGCTCT
GTACCTGCCCGGGCGGCCGCTCG 3. SEQ ID No. 3 (Regulatory gene (666bp))
ACCGATGAACATTCCAACGACTCGCCCGAATCGTGGGNTGGCGAGGGCC
CCGACAGTTCTCCCGTCGCCGACGTCGAGGTGAAGATCCACGACATTTCC
CATCCGCTCGCCATGGCCTCCGCCAAAGCCTTCCACTTCAATATGGTCGC
TCCTCACGATGCGGACCTGTCGATGGGAGACGTAACGCCCAAGGTCGAA
GAAGTGGACGACGCGGATGATTTACAAAGTATCAAACCTATGGGTGTGG
ATCCGCTGGCCAATGCGGACTCTACTCATCTGGATTCCACGGCTCTTCCC
GTCAACGTTCCACGGAAACGTGGACGACCACGCAAACATCCTCTTCCAG
CTCCCGGAGGTCAAGTGAAAATCACCAAAGGTCGATCCAAGACGGGCTG
CATAACGTGTCGACGACGGAAGAAGAAATGCGACGAGACCAAGCCAGC
GTGCCTAAATTGTCAGAAAAATGCCGTCGTGTGTGAAGGTTATCCGCCAA
AGGAGATCTGGAAGAGTGGGAAACAGAAGCAGGAAGATGCAGCTGCCC
GATGCCAGACGATGATCTCTCGTGCCCTCCTTTCTGATCGATGGAATCGA
AAGCGATATTGACCGACGCTTTCTGGATCATTTTGGGACCTCGGGCGNGA
NCACCTTATCACTAATGAATTTGCG 4. SEQ ID No. 4 (3-oxoacyl synthase (846 bp))
CGAGGAATGCGAACGCTGGGGTTCACTTCGATCAGGNCACCTTTAGCGG
TGTGAATGTAGATCTGAAGTTTACCGGCCTTGTTGACGGGCGAATCGAGG
AGGGTGAGGAGACACTGATGGGTAATATCCGGTCGAGCCTCGCTGATGT
CTCTGTTCATCTTGCGCATCACACCGATATGCTCGTCGCTGTTGAGCAAG
GAGTATTTCTCATCACGGTTGGTGCCGCTGCGTCCGCCATGAGAGGCGCG
GAAAGTTTCCAAGCTTGCATGAGACAGGACGACGATCAAGCGCTGGGTC
TCTTTATCGTGGGCAGAGATGGGGACGATGTTGCTCGGCGACCAACTGAG
GCAGTTCGGGAGGAGGGCAAGACTGGGTCCTGGCACGCTTTCTCCTTCCT
GCTACTTGAACAGAATCCGACATATTGAACCGATGAACCAATTGAAGAC
TTTTTTTATATAAAATAAAAAAGGAGAGTATTATATGTAATTCGAGACTC
GGGACCGATAAGAAGAAATCGAGGGAGGAGGAGAAAAGACNGACGACAG
ACGATTGAGAAGAGCGACAAACGGTAATAAAGGAAGATCCCGAGAGGC
GCANAGAGAANGAAGCGGTTGCAGGATAACTGCAGTCCANGATGANGG
GATTCAAGGGGGATGTTTGTCGCTTGCTTAACCCCGGACTGCCGCGCGTC
AATATATGATCCGCGCTGAGCACTTGAANTCACCGTGANTANTGGTTTGG
ACTAANTGNGAATGNANTGTCTGGAATGTCTCATCCCAANACGACTAAG
AGCGGNATNGCATCATATGTGNNTCNTCACGACGGCATTATACCACCGG
AGGTGTG APPENDIX 1-continued 5. SEQ ID No. 5 (Trichodiene oxygenase (572 bp))
CAGACTGTCATTGTATGGGCTGTCGTTTCAGTTCCCNTTNNCACAATGGT
AATGTATTCATGAAGAACCCTANCCTCGGTGACATCAGGGGTATCGGGG
GCTTTGGCGACCATTTCCTGGAAAAGCGCCGGTTCCTGGGAGAGTCTGTT
TTTCTCAAAGTCTAGCTTCGCCTCTTCTTCGTTCTCCCACATGAAGTTCA
CCTCCTGGGCACATTTCATTCGAAATGCAATCACAGGGAGCAACTTGGGA
TAAACCCGCTTGACCCACTTCATTCCCATGCTCGCCAGAAGAGGGAAAAA
TCCCGGAAGATGCCGGGCGATCATTCCGATCTCGACGAGGTTCTTAATTG
TTTCACTCCATATAGGGACCATCTCGGGGTCGTCTAGGTAGTTGAACGCA
CGGAAGCTCGTATAAGAGGTGATAATGTCGGCGGTGAAACAGTTGAATG
CGACGTGTACTTTTAGGGGCTCCCCCGAGTGAGCATACTCGCTCAACCGG
GTATTCAGTTTTGAAGTTTACTCTGAATGAGTGACTGAATACGCTGTAC
CTCGGCCGCGACCACGCTAATCACTAGTGAATTC 6. SEQ ID No. 6 (Acyl CoA dehydrogenase (670 bp))
ACTATCCACTTGATGGAATTCACAACTTCTTCTCCCTGTTTCCCTCTCTA
AAGCCAAAAACAGACCCCGCAATCTTTCTCATCTGGATTTCTTCCGACCC
CTCCGTAATTCGATACCGTCTAAAATGACGATAAATGTGCTCGAATAGAT
AATGGCGCGAGTATCCATCTCCCCCGTGGATCTGAATCGCCCTATCCGCC
GCCTCGCAAACTAATCTATTAGCCCAAAAATTACACATTGCGACCTCATC
GCCCAGTTTCTTCTCGATCTCCACCCAAGGCTTTCTCCCCTCGCTCTCCG
CCTCCCCAGCTACCTGATCCATGTCCACACTAGTCTTCAGAATCAGCAGT
CGGAGCATCTCGACCTGCGTCACCAACTCAACGACTGGGAACTGAATGCC
CTGGTTCTCGGACAGACCCTTTCCGCCCCAAATTTTCCTGTTCTTCGCGC
GCTCAATGCTCCGATCCAGGCAGAACTTTGCCGCACCGCATGAATTGGCC
GCCTGTCGCAGTCGATTTTCATACATGAATGTCTGCGCGATCGCTAGTCC
CTCGCCAACAGTTCCTAGCACAGCCTCAATTGACACAAAAACCCGATCTA
AATTTACGGTCGCATGATCGGTCGGCATATTCATCGGCCATTCGTAACTA
CGATTTCACCCCCTTCGTCT SEQ ID No. 7 (Polyketide synthase 2179
nucleotides):
TCGAAGGCAATTGCCAATGGAGAATCAAATGGCACAAGTCGCAATTCCAC
TTCGCAGTTGGATCCCGGAAAGCCGTGTTTTCATTCTTTCGGCATTTGAT
GAGGCTGGTTTGGACCGAAACGCGATGTCCATGATATCTTACCTCGAATC
ATTGAAACTCTCCGGAGATCCTGATCTGGAAGAAGCGTTCATGAGCGACC
TATGTCATACACTAAACGCAAAACGCACAATGTTTGATTGGCGCAGCTAC
CACGTCGCTGACACCATCGAAAACCTAAAAAAGTCGCTTCGGAATATCCG
CCCATATCGTCGATCGACAAGCTCGAAAGCCGTCCGTTTTATATTCACGG
GCCAAGGAGCGAATTGGGCTGGCATGGCCCAAGATCTCTTACTTTACCCA
TTGTTTCGACAACGGATCCAAGAAGCTGCAATGTTCTTGGGAGAAATTGG
ATGCGAGTGGGATCTTTATGGTATAGTCTTGTCCATTCCTTTTCTTAATC
CTTTTTTTTGTCTTTATTTCCTCCTCTCTCCCCTCAAATTATTGGGTGAC
GCCGAATAACCAAAAATTTAGACCGAATCAGCTCACAGCACGGTGACCTA
AACGAGCCCACTTTTGCGCAATCCTCCTGTCTGTGTAGCCGTGCAGATTGCGTT
GGTAGACTTGCTTCATAGCTGGAAGGTGACGCCAACAACGGTAGTAGGAC
ATTCGTCCGGCGAAATTGCAGCAGCGTATTGTGCGGGAAAAATCTCACGT
CAAGCAGCATGGAAAATCGCCTACTGTCGAGGACAGGTTTGTGCAAAACA
GACACACGAAGATGGCCGCATGCTCGCAGCGGCTATGCCTGCACAGGAA
TTGGAACGACTGTTAGCTCGTTTGAACAAAGGTCTATGCTCTGCGGTTCA
GGTCGGATGTTATAACAGCCCCAAGAACTTGACCCTGACAGGCCAACAC
GAGAGCATTCTTCAGGTCAAGGGCGAGTTAGACGAAGCGGGTGTGCTAA
ACCGTTTACTTCCAGTTAAGGTTGCTTATCACTCGAAATTCATGCGAGAA
GTCGCTCCAGAGTACTTAGAGCTCCTCGGGGACCTGGATTTCGGTGACAA
GATGACCGACCATGCCAAAGTTACTATGATATCCTCGGTTACGGGACGAC
ATGCACTCGCAGGGGAGGTTGAGAGTCCTTCGTACTGGGTTGATAATCTG
ATCTCACCTGTCCGTTTCTCTACTGCGCTTCTCACATCCATGCAAACACA
AAGTCAAAAGTCACCCAGCGATAACGCACTGATTGAAATCGGACCTCATT
CTACTCTCCGCACCGCCATCAATGAGACCCTTGCGGATCAACCTACACTG
CAGCCGTTTCAATACGGTAGTCTGCTCAAGCGATATGAGACTGACGGAA
CGACAAGCCTGCGCACATTCGATTTGTTGACCTCTTATGGCTATGATGTT
AGCCTGGCTTCTGTTAATGATCCTCGATCAAAAATTAAGAAAGCTCCTCA
TATGATAACGGATCTTCCGCCTTACTCCTTTGACCACTCACGGTCGGTTC
GCGGCCAGTCTCGAAGAATCAAAAACATCAAGTTTCCAGCGTACGAACGC
CATGAGCTCCTTGGTGCGCCAGTTGAAGATACAAACAAATTTGAGCAAC
GATGGAGGAACATCATTAGACCGGACGATATTACATGGTTGCGCATGAA
CAGAGTGAGTACTTCCTATAAAATTATGAGCCCATCTAACGTGAGCCAGA
TGGATGGAAGTATCCATTTCCCCGGAGTCGCCTACCTTTTGATGGCCATG
GAGGCCATAATGCAGCGAACTGGGATGACAGAATGTGTCACCGGCATTA
GGATTGGCAATGTGGCTATGCTGGCCCCTTTGCCTGTTCCCGACACCCCA
GAAGGTGTCAGAGTCATCTTTTCGATCTACCCGATGAACGAGTCAGCCCG
GGCCACAGATGACTGGTGCACCTTCAGAGTTATCTCCCATGAAGGGGTTG
AAAATTCTTGGATTGAGCACTGCGTTGGTTCAGTTCGTATAGAAACGGGA
GAGCAGAGGATATCCGCCCTCCTGTTGACAGCCAGTTGTCAATATGTTC
TGAAGCCGTCGATATAAACCAAATGTATCGAGACTTCGCCTCTGCGGGA
ATGGAATTTGGCGACTTCCTGAAAAACATTCGAAGCAT SEQ ID No. 8 Aspergillus carbonarius ketosynthase
(KS) region of the pks gene sequence (314
nucleotides):
GAATTCACTAGTGATTGCGAATGGGTATGCGCGGGCGAAGCCATTGGC
TGTCTAATACTCAAGCCATTGAAGAATGCTGTTCGAGATGGGGATCATAT
TTACGCTATCATCCGAGGATCAGGGTCTAACCAGGACGGGAGAACCCCC
GGAATCACGCTCCCTAGTGAGGTGGCGCAAGAGGCTTTGATACGACGCG
TATATCAAATGGCATGTCTTAATCCAGCAGATACCGACTTCGTTGAGGCC
TACGGCACCGGCACAATNGAATTCCCGCGAGCCGCCAGGCGGCCGGGAG
CTGGAACTCGGGCCCATG SEQ ID No. 9 P. verrucosum ketosynthase (KS)
region of the pks gene sequence (311 nucleotides):
CATGGGCCCGAGTTCCTGCTCCCGGCCGCCTGGCGGCCGCGGGAATTCCA
TTGAATGGGTATGCGCGGGGCGAGGCAGCTGGCTGTCTTATCCTTAAACC
CCTAGCCAAGGCGTTGCACGACCGGGACAACATCAGGGCCGTAATACGA
GGAACCGGTTCCAATCAAGACGGGCGCACCGCAGGGATAACACTACCAA
ATGGGGCAGCCCAAGAAACCTTGATTCGGAGCGTCTATACACGGGCTGG
TCTGGATCCCTCCGAAACAGATTTTGTGGAGGCCTACGGCACCGGCACAA
TCACTAGTGAATTC

REFERENCES

Burdaspal, P. A. and T. M. Legarda (1998). Ochratoxin A in roasted and soluble coffees marketed in Spain. Alimentaria, 35: 103-109.

Burdaspal, P. A. and T. M. Legarda. (1999) Ochratoxin A in wines and grape products originated from Spain and other European countries. Alimentaria, 36: 107-113.

Dietrich, D. R., C. Schlatter, l. Studer-Rohr and J. Schlatter. (1995) The Occurrence of Ochratoxin A in Coffee. Food and Chemical Toxicology, Volume 33, Issue 5, May 1995, Pages 341-355.

Edwards, S. G., J. O'Callaghan and A. D. W. Dobson (2002) PCR based detection and quantification of mycotoxigenic fungi. Mycol. Res. 106: 1005-1025.

Geisen, R. (1998) PCR methods for the detection of mycotoxin producing fungi. In Applications of PCR in mycology (P. D. Bridge, D. K. Arora, C. A. Reddy, and R. P. Elander, eds): 243-246. CAB International, Wallingford.

Jorgenson, K. (1998) Survey of pork, poultry, coffee, beer and pulses for ochratoxin A. Food Addit Contam. 16: 75-78.

Kuiper-Goodman, T. (1996) Risk assessment of ochratoxin A: an update. Food Addit. Contam. 13 (suppl): S53-S57.

Pittet, A. (1998) Natural occurrence of mycotoxins in food and feeds-an updated review. Rev. Med. Vet 149: 479-492.

Scientific Committee for Food (1996). Opinion on aflatoxin, ochratoxin A and patulin, expressed on 23 Sep. 1994. Reports of the Scientific Committee for Food. 35th series. Luxembourg Visconti, A., M. Pascale and G. Centonze. (1999) Determination of ochratoxin A in wine by means of immunoaffinity column clean-up and high-performance liquid chromatography, Journal of Chromatography A, Volume 864, Issue 1, 9 Dec. 1999, Pages 89-101.

Visconti, A., M. Pascale and G. Centonze (2000) Determination of ochratoxin A in domestic and imported beers in Italy by immunoaffinity clean-up and liquid chromatography. Journal of Chromatography A, 888: 321-326

Wolff, J. H. Bresch, C. Cholmakov-Bodechtel, G. Engel, M. Garais, P. Majerus, H. Rosner, R. Scheuer. (2000) Ochratoxin A: contamination of foods and consumer exposure. Arch. Lebensmittelhyg. 51: 81-128.

Zimmerli, B and R. Dick. (1996) Ochratoxin A in table wine and grape juice: occurrence and risk assessment. Food Addit. Contam. 13: 655-668.

The invention claimed is:

1. An assay for the detection of an *Aspergillus ochraceus* strain producing ochratoxin A comprising the steps of:
   obtaining a sample;
   extracting DNA from said sample;
   using said extracted DNA as a template to amplify DNA sequences in the presence of an oligonucleotide primer derived from the PKS nucleic acid sequence of SEQ ID No. 7; and
   analysing the amplified sequences for the presence of the PKS nucleic acid sequence of SEQ ID No.7
   wherein an *Aspergillus ochraceus* strain producing ochratoxin A is identified by the presence of a PKS nucleic acid sequence comprising SEQ ID No. 7.

2. The assay of claim 1 wherein the oligonucleotide primer is selected from any one or more of SEQ ID No. 20, SEQ ID No. 21, SEQ ID No. 22 and SEQ ID No. 23.

3. An assay for identifying an *Aspergillus ochraceus* strain expressing a PKS gene comprising the steps of:
   obtaining a sample;
   extracting RNA from said sample;
   synthesising complementary DNA (cDNA) from said extracted RNA;
   using said extracted cDNA as a template to amplify cDNA sequences in the presence of an oligonucleotide primer derived from the PKS nucleic acid sequence of SEQ ID No. 7; and
   analysing the amplified sequences for the presence or absence of the PKS nucleic acid sequence of SEQ ID No. 7,
   wherein an *Aspergillus ochraceus* strain expressing a PKS gene is identified by the presence of a PKS nucleic acid sequence comprising SEQ ID No. 7.

4. The assay of claim 3 wherein the oligonucleotide primer is selected from any one or more of SEQ ID No. 20, SEQ ID No. 21, SEQ ID No. 22 and SEQ ID No. 23.

5. An assay for the detection of an *Aspergillus ochraceus* strain producing ochratoxin A comprising the steps of:
   obtaining a sample;
   extracting DNA from said sample;
   using said extracted DNA as a template to amplify DNA sequences in the presence of a pair of oligonucleotide primers wherein said pair of oligonucleotide primers are selected from the group consisting of (i) the pair of oligonucleotide primers of SEQ ID No. 20 and SEQ ID No. 21, and (ii) the pair of oligonucleotide primers of SEQ ID No. 22 and SEQ ID No. 23; and
   analysing the amplified sequences for the presence or absence of the PKS nucleic acid sequence of SEQ ID No.7
   wherein an *Aspergillus ochraceus* strain producing ochratoxin A is identified by the presence of a PKS nucleic acid sequence comprising SEQ ID No. 7.

6. An assay for identifying an *Aspergillus ochraceus* strain expressing a PKS gene comprising the steps of:
   obtaining a sample;
   extracting RNA from said sample;
   synthesising complementary DNA (cDNA) from said extracted RNA;
   using said extracted cDNA as a template to amplify cDNA sequences in the presence of a pair of oligonucleotide primers wherein said pair of oligonucleotide primers are selected from the group consisting of (i) the pair of oligonucleotide primers of SEQ ID No. 20 and SEQ ID No. 21, and (ii) the pair of oligonucleotide primers of SEQ ID No. 22 and SEQ ID No. 23; and
   analysing the amplified sequences for the presence or absence of the PKS nucleic acid sequence of SEQ ID No.7
   wherein an *Aspergillus ochraceus* strain expressing a PKS gene is identified by the presence of a PKS nucleic acid sequence comprising SEQ ID No. 7.

* * * * *